United States Statutory Invention Registration [19]

[11] Reg. Number: H424

Martin et al. [43] Published: Feb. 2, 1988

[54] METHOD OF SYNTHESIZING THE BISMALEIMIDE OF DIMER DIAMINE VIA CYCLODEHYDRATION

[75] Inventors: Eugene C. Martin; Albert A. De Fusco, both of Ridgecrest, Calif.

[73] Assignee: The United States of America as represented by the Secretary of the Navy, Washington, D.C.

[21] Appl. No.: 703,590

[22] Filed: Feb. 21, 1985

[51] Int. Cl.[4] ..... C07D 207/452
[52] U.S. Cl. ..... 548/522
[58] Field of Search ..... 548/522

[56] References Cited

U.S. PATENT DOCUMENTS

| | | | |
|---|---|---|---|
| 4,130,564 | 12/1978 | Haug et al. | 260/326.26 |
| 4,138,406 | 2/1979 | Balasfalvy | 260/326.26 |
| 4,154,737 | 5/1979 | Orphanides | 260/326.26 |
| 4,581,461 | 4/1986 | Rossi et al. | 548/406 |

OTHER PUBLICATIONS

Fieser and Fieser, *Reagents for Organic Synthesis*, vol. 5, (1975), p. 342.

Strathmann, et al, Chem. Abstracts, vol. 86 (1977), entry 6216x.

*Primary Examiner*—Richard D. Lovering
*Assistant Examiner*—J. E. Thomas
*Attorney, Agent, or Firm*—William C. Townsend; W. Thom Skeer

[57] ABSTRACT

The bismaleimide of dimer diamine is synthesized using N,N'-dicyclohexylcarbodiimide and 1-hydroxybenzotriazole.

10 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD OF SYNTHESIZING THE BISMALEIMIDE OF DIMER DIAMINE VIA CYCLODEHYDRATION

BACKGROUND OF THE INVENTION

1. Field of the Invention

This invention relates to the field of polymer chemistry. More particularly, this invention relates to the synthesis of the bismaleimide of dimer diamine. Still more particularly, but without limitation thereto, this invention relates to the synthesis of bismaleimide of dimer diamine using N,N'-dicyclohexylcarbodiimide and 1-hydroxybenzotriazole.

2. Description of the Prior Art

Previous methods for synthesizing the bismaleimide of dimer diamine and other aliphatic bismaleimides, relied upon dehydration of the precursor bismaleamic acid with acetic anhydride, acetic anhydride/sodium acetate or acetic anhydride/triethylamine in an analogous fashion as in the synthesis of aromatic substituted maleimides. However, these reagents continually provide a low yield, 9–41%, of the aliphatic bismaleimide product.

Other general methods which, for example, require heating of the precursor maleamic acids to high temperatures in order to remove water, again result in low yields of maleimide products.

Some work has been done on the synthesis of very low molecular weight, monofunctional aromatic substituted maleimides using N,N'-dicyclohexylcarbodiimide and 1-hydroxybenzotriazole co-reagents. However, no work has been described on the synthesis of polyaliphatic substituted bismaleimides from precursor bismaleamic acids using these co-reagents. A process has also been developed for very low molecular weight monofunctional aliphatic maleimides. This process uses a mineral acid for cyclodehydration followed by elimination of hydrochloric acid to form the maleimide. This process is not feasible with dimer diamine since the polymeric backbone contains unsaturation which is susceptible to addition by hydrochloric acid just as the maleimide double bond is.

The present invention provides a means by which the bismaleimide of dimer diamine can be synthesized in 38–56% yield by a mild method involving cyclodehydration of precursor bismaleamic acid.

SUMMARY OF THE INVENTION

An object of this invention is to provide a means for synthesizing a low molecular weight, difunctional prepolymer that can be polymerized to a thermally stable polymer.

A further object of this invention is to provide an improved method of synthesizing the bismaleimide of dimer diamine in high yield.

These and other objects have been demonstrated by the present invention wherein the bismaleimide of dimer diamine is synthesized using N,N'-dicyclohexylcarbodiimide and 1-hydroxybenzotriazole.

DESCRIPTION OF THE PREFERRED EMBODIMENT

Aromatic substituted bismaleimide prepolymers have received much attention as being heat resistant polymers after cure and can be used in composite formulations because of their exceptional thermal stability after cure. Prepared from parent aromatic diamines and maleic anhydride, these prepolymers are usually solids at room temperature and are cured with solvents and at temperatures above 200° C. Synthesis of aromatic maleimides involves the cyclodehydration of the precursor maleamic acids with N,N'-dicyclohexylcarbodiimide (DCCD) and 1-hydroxybenzotriazole (HOBT) co-reagents.

For processing and fabrication purposes, it would be advantageous to cure bismaleimides without solvent and at lower temperatures. Aliphatic substituted bismaleimide "monomers" or prepolymers are a superior substitute for the aromatic systems since selected moderate molecular weight liquid diamines leads to liquid bismaleimides. This eliminates the need for a solvent and also might broaden the applications of these materials.

The DCCD/HOBT co-reagents are particularly useful for the mild synthesis of the bismaleimide of dimer diamine from the parent diamine and maleic anhydride. Yields on moderate-scale repetitive runs are in the range of 38–56% of exceptionally pure material, as is shown by Table 1.

TABLE 1

| Conditions Temp, °C./Time, Hrs. | Yield of Bismaleimide |
|---|---|
| 3–5/5 then 25/16[a] | 50 |
| 5–10/4 then 25/16[a] | 42 |
| 5/7 then 25/16[a] | 38 |
| 0/4 then 25/16[a] | 56 |
| 0/4 then 25/6[b] | 0 |

[a]tetrahydrofuran was used as solvent
[b]ethylene dichloride was used as solvent Ether solvents are suitable for use in this invention, but it is clear from the data that tetrahydrofuran (THF) is preferred over, for example, ethylene dichloride as a solvent.

Reaction of dimer diamine with maleic anhydride gives the bismaleamic acid, which is used directly from its reaction mixture. Adding twofold molar amounts of DCCD and HOBT to the bismaleamic acid in tetrahydrofuran affords crude bismaleimide, precipitated N,N'-dicyclohexylurea (DCU), and HOBT. Maleimide formation presumably occurs via the activated ester derived from the alcohol HOBT and the carboxyl group of maleamic acid.

Table 1 lists the highest possible yields via this method. Considerable amounts of "monomer" appear to be lost during isolation and purification even though monitoring the reaction mixture by proton nuclear magnetic resonance (NMR) indicates complete conversion of bismaleamic acid to bismaleimide. The explanation for the loss of product can be gained through gel permeation chromatography (GPC) and carbon NMR spectroscopy.

Dimer diamine is manufactured from dimer acid, a mixture of mono, di and trifunctional oligomeric, aliphatic and carboxylic acids, which in turn is produced from thermal cyclization of unsaturated fatty acids via a Diels-Alder process. The nature of these materials reflects the reasons why the yields of bismaleimide are limited and cannot be improved without sacrificing the quality of the final product.

Comparison of the GPC trace for dimer diamine and pure bismaleimide of dimer diamine indicates that the latter compound is nearly "monomeric" with a polydispersity ($\overline{M}_W/\overline{M}_N$) of 1.02. Differences in these GPC traces are the result of product fractionation during isolation and purification.

Support for fractionation is also given through carbon NMR spectroscopy where the olefinic region of dimer diamine shows many peaks whereas the bismaleimide NMR shows only two olefinic carbons for the polymer chain as well as the maleimide olefin. Isolated as a single "monomeric" molecule, the product bismaleimide has a well defined molecular weight of 707 gm/mole (from proton NMR peak integration) instead of a broad distribution of molecular weights resulting from an agglomeration of many different molecular weight fractions as in dimer diamine.

Since the purification of crude bismaleimide presumably involves extraction of one molecular weight fraction of the cyclodehydration products from bismaleamic acid, it is very unlikely then that higher yields of pure bismaleimide can be obtained. High and mostly low molecular weight materials are undoubtedly removed from bismaleimide during purification. Fractionation of dimer diamine before use is not feasible since several methods for this purpose have been studied and found ineffective.

The bismaleimide of dimer diamine may be prepared by carrying out the procedure set forth in the following specific example.

EXAMPLE

Pre-Preparation

The dimer diamine is heated to 80° C. in vacuum (27 in Hg) for 18 hours before use. Maleic anhydride is purified as follows: the crude material (180 g) is diluted to 400 ml with chloroform while warming followed by filtration and addition of 40 ml of heptane. Cooling followed by filtration affords 169.2 g pure material (mp 47°-51° C.). Tetrahydrofuran (THF) is distilled under $N_2$ from potassium in the presence of naphthalene while a green color remains.

N,N'-dicyclohexylcarbodiimide (DCCD) is used without further purification. The 1-hydroxybenzotriazole (HOBT) is dried by heating at 100° C. under vacuum (27 in Hg) to a constant weight.

Preparation of Bismaleimide of Dimer Diamine

Purified maleic anhydride (17.7 g, 0.1805 moles) is weighed into a one liter, 4-neck, reaction flask equipped with a mechanical stirrer, a 250 ml dropping funnel, and a $N_2$ inlet/outlet. After the flask is purged with $N_2$ for a short while, 100 ml of dry THF is added under positive $N_2$ flow. The dropping funnel is charged with a solution of 50.4 g (0.0894 moles) of dimer diamine and 125 ml dry THF under positive $N_2$ flow.

The dimer diamine solution is added dropwise at ambient temperature over a two hour period. After stirring for an additional two hours, the mixture is cooled to 0° C. and 24.4 g (0.1806 moles) of HOBT along with 100 ml of dry THF is added in one portion under positive $N_2$ flow.

A solution of 37.3 g (0.1808 moles) of DCCD in 100 ml of dry THF is then added dropwise over a 15 minute period. At the end of the addition period, the reaction mixture is a light yellow solution which precipitates a solid (DCU) after stirring for 10 minutes at 0° C.

After two hours of stirring a one ml aliquot is extracted, filtered and the THF evaporated. Analysis of the residue by proton NMR ($CDCl_3$) reveals the presence of unreacted bismaleamic acid (δ6.60, 2H, CH=CH). The reaction mixture is then allowed to come to room temperature without stirring. After standing at room temperature overnight, stirring is continued again and another one ml aliquot is extracted. Proton NMR ($CDCl_3$) reveals only the presence of the bismaleimide and no bismaleamic acid.

The reaction mixture is then filtered and the filtrate evaporated to give an oil/solid mixture which is taken up in 300 ml of cyclohexane and stored at −5° C. overnight. Any aliphatic solvent will suffice, with cyclohexane being preferred. The cyclohexane mixture is centrifuged at 3500 rpm for 20 minutes. The resulting cloudy cyclohexane supernatant liquid is decanted, filtered and evaporated to give a cloudy oil. The remaining solid from centrifugation is air dried and amounts to about 80% of the original amount of HOBT.

The cloudy oil product is dissolved in a minimum amount of benzene and chromatographed on 125 g of silica gel. Table 2 outlines the procedure for chromatography along with the fraction identities and their amounts after evaporation of solvent.

TABLE 2

| Fraction | Solvent | Product |
|---|---|---|
| 1 (200 ml) | benzene | 4.4 g of thick syrup |
| 2 (200 ml) | benzene | 13.8 g of pure bismaleimide |
| 3 (250 ml) | 3% ethyl acetate/ 97% benzene | 12.5 g of pure bismaleimide |
| 4 (250 ml) | 5% ethyl acetate/ 95% benzene | 2.4 g of pure bismaleimide |
| 5 (300 ml) | 7% ethyl acetate/ 93% benzene | 0.7 g of cloudy oil |
| 6 (300 ml) | 10% ethyl acetate/ 90% benzene | 0.4 g of cloudy oil |

The purity of the fractions from chromatography are determined by IR spectroscopy. Fractions 2, 3 and 4 (Table 2) are pooled and amount to 28.7 g (44.4%) of pure bismaleimide of dimer diamine.

Fraction 1, after evaporation, gives 4.4 g of a thick syrup which turns to rubber upon prolonged exposure to air. Fractions 5 and 6 are evaporated to give oils (0.7 g and 0.4 g respectively). They show the presence of benzotriazolelike signals in their $^1H$ NMR and are discarded.

The IR spectrum of bismaleimide (fractions 2, 3 and 4) shows peaks at 3000 (maleimide CH), 2850, 2780, 1680 (maleimide CO), 1450, 1425, 1390, 1350, 1110, 825 and 692 $cm^{-1}$.

An $^1H$ NMR ($CDCl_3$) spectrum shows peaks at δ6.8 (2H, s, CH=CH), 3.6 (2H, t, $NCH_2$), 2.0–1.4 (ca. 86H, br s, CH and $CH_2$) and 1.0 (6H, s, $CH_3$) A C-13 NMR ($CDCl_3$) shows peaks at δ172 (C=O), 158 (C=C), 155 (maleimide olefin), 139 (C=C) and 40–19.5 (CH, $CH_2$ and $CH_3$).

This invention has been described in detail with particular reference to certain preferred embodiments thereof, but it will be understood that variations and modifications can be effected within the spirit and scope of the invention.

What is claimed is:

1. A method of synthesizing a bismaleimide of dimer diamine, comprising the steps of:

(A) adding maleic anhydride and dimer diamine to form a first solution;

(B) cooling said first solution to a temperature of about 0° C.;

(C) mixing 1-hydroxybenzotriazole to said first solution to form a second solution maintained at a temperature of about 0° C.;

(D) adding N,N'-dicyclohexylcarbodiimide to said second solution to form a third solution maintained at a temperature of about 0° C.;

(E) precipitating a solid from said third solution at a temperature of about 0° C.;

(F) filtering said third solution to yield a filtrate;

(G) evaporating said filtrate to yield an oil/solid mixture;

(H) placing said oil/solid mixture in solution;

(I) separating said solution to yield a supernatant liquid;

(J) decanting and filtering said supernatant liquid;

(K) evaporating said supernatant liquid to yield a crude product; and (L) purifying said crude product by chromatography to yield a pure product.

2. The method of claim 1 wherein the maleic anhydride of step A is in solution with an ether solvent.

3. The method of claim 2 wherein said ether solvent is tetrahydrofuran.

4. The method of claim 1 wherein the dimer diamine of step A is in solution with an ether solvent.

5. The method of claim 4 wherein said ether solvent is tetrahydrofuran.

6. The method of claim 1 wherein the N,N'-dicyclohexylcarbodiimide of step D is in solution with an ether solvent.

7. The method of claim 6 wherein said ether solvent is tetrahydrofuran.

8. The method of claim 1 wherein the solution of step H is comprised of an aliphatic solvent.

9. The method of claim 8 wherein said aliphatic solvent is cyclohexane.

10. The method of claim 1 wherein step I is carried on by centrifuging.

* * * * *